United States Patent
Boese et al.

(10) Patent No.: US 8,054,941 B2
(45) Date of Patent: Nov. 8, 2011

(54) METHOD FOR THE PRODUCTION OF ANGIOGRAPHY RECORDINGS

(75) Inventors: Jan Boese, Eckental (DE); Yu Deuerling-Zheng, Erlangen (DE); Michael Zellerhoff, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 127 days.

(21) Appl. No.: 12/507,818

(22) Filed: Jul. 23, 2009

(65) Prior Publication Data

US 2010/0027751 A1 Feb. 4, 2010

(30) Foreign Application Priority Data

Jul. 30, 2008 (DE) .......................... 10 2008 035 549

(51) Int. Cl.
- H05G 1/64 (2006.01)
- H05G 1/60 (2006.01)
- H05G 1/58 (2006.01)
- G01N 23/083 (2006.01)

(52) U.S. Cl. .................... 378/98.12; 378/98.11; 378/62; 378/63; 378/98.8; 382/130

(58) Field of Classification Search ............... 378/4–20, 378/62, 63, 91, 95, 98.8, 98.11, 98.12, 114–116, 378/210; 600/407, 411, 413, 425, 428, 431; 382/128, 130–133
See application file for complete search history.

(56) References Cited

U.S. PATENT DOCUMENTS

| | | | |
|---|---|---|---|
| 4,483,342 A | | 11/1984 | Pfeifer |
| 4,543,604 A * | | 9/1985 | Grosse ..................... 378/98.12 |
| 4,581,635 A | | 4/1986 | Franke |
| 4,611,340 A * | | 9/1986 | Okazaki .......................... 378/95 |
| 5,095,906 A * | | 3/1992 | Ema .............................. 600/407 |
| 5,412,562 A * | | 5/1995 | Nambu et al. .................... 378/10 |
| 5,459,769 A * | | 10/1995 | Brown ............................. 378/4 |
| 6,005,917 A * | | 12/1999 | Andersson et al. ........ 378/98.12 |
| 7,024,027 B1 * | | 4/2006 | Suri et al. ...................... 382/130 |
| 2004/0127789 A1 * | | 7/2004 | Ogawa .......................... 600/425 |
| 2007/0195932 A1 * | | 8/2007 | Nakaura et al. ............ 378/98.12 |
| 2008/0240363 A1 | | 10/2008 | Grebner et al. |

FOREIGN PATENT DOCUMENTS

| DE | 3215552 C1 | 10/1983 |
|---|---|---|
| DE | 10 2005 012 700 A1 | 9/2006 |

OTHER PUBLICATIONS

Patrick Kurp, Siemens Medical, "Axiom Artis FD Systems, DynaCT-A breakthrough in Interventional 3D Imaging", Reprint from Medical Solutions, Jan. 2005, pp. 46-51, Erlangen, Germany.

* cited by examiner

Primary Examiner — Anastasia Midkiff

(57) ABSTRACT

The invention relates to a method for the production of angiography recordings. First, a mask image is recorded with a first modality. A contrast medium is injected after the first recording. A control image is recorded with a second modality after the injection of the contrast medium. A spreading of the contrast medium is determined based on the images and the control of subsequent recordings is analyzed. A recording criterion is checked to determine whether the recording criterion has been achieved. If it has not been achieved, the control image is repeatedly recorded for repeatedly determining the spreading of the contrast medium. If it has been achieved, a contrast image is recorded with the first modality and the mask image and the contrast image are processed and analyzed.

16 Claims, 4 Drawing Sheets

METHOD FOR THE PRODUCTION OF ANGIOGRAPHY RECORDINGS

CROSS REFERENCE TO RELATED APPLICATIONS

This application claims priority of German application No. 10 2008 035 549.6 filed Jul. 30, 2008, which is incorporated by reference herein in its entirety.

FIELD OF THE INVENTION

The invention relates to a method for the production of angiography recordings. The aim of angiography is to map the vascular system for diagnostic purposes. The generation of angiographic images of the vascular system generally requires two recordings of the tissue under examination: one recording without a contrast medium, a so-called mask recording, and a second recording with a contrast medium in the vessels of the region to be recorded, a so-called contrast recording.

BACKGROUND OF THE INVENTION

The recordings can be produced with the aid of various recording methods:
Magnetic resonance tomography (MR angiography),
Computed tomography (CT angiography),
3D angiography with C-arm angiography devices and/or
X-ray projection (DSA, digital subtraction angiography).

The first three methods are cross-sectional or volume imaging methods, and the fourth method is a 2D projection method.

In addition to the imaging of vessels during angiography, the visualization of contrast medium accumulation in tissue, for example in order to measure cerebral blood volume (CBV), has an increasing role to play.

Since the contrast medium spreads out dynamically within the tissue and the vascular system, the point in time at which the second recording, the contrast recording, is made is of central importance.

Owing to the relatively small amounts of contrast medium in the tissue, an observation by a human analyzer is more difficult and the operating experience on the basis of which the timing of the contrast recordings could be set is still limited.

The second recording of an angiography, the contrast image, is usually triggered manually by the operator of the device, for example a radiologist, as described for example in U.S. Pat. No. 4,483,342, or after a delay that can be varied according to the injection, as described in U.S. Pat. No. 4,581,635. The delay is in turn set by the operator on the basis of empirical values.

DE 32 15 552 C1 describes a method for 2D projection images in which the optimal mask image, which lies shortly before the rise of the contrast medium by one pixel along the time-contrast medium curve, and the optimal contrast image, the image with the maximum contrast medium density, are determined automatically. The points in time of the two sought images are found on the time-contrast medium density curve with threshold methods.

U.S. Pat. No. 4,581,635 A describes in general terms x-ray angiography systems and digital subtraction angiography. This does not include the triggering of recordings by automatic tracking of bolus arrival at a target location, which forms the main part of our invention.

U.S. Pat. No. 5,459,769A describes a method of determining the optimal start time for the recording, but this method differs from our invention as follows:
1. Bolus arrival is monitored manually. We have described a fully automatic method.
2. Bolus arrival is determined with a time-contrast curve by means of a user-defined region of interest (ROI), whereas our method takes the whole image into consideration, thus making automatic calculation possible.
3. As the recording is linked to (many) user interactions, the method in D2 cannot be considered to be a triggering, which is the main idea of our invention.

SUMMARY OF THE INVENTION

The object on which the invention is based is to embody a method of the type described in the introduction such that an optimal triggering of the second recording for angiography or blood volume measurement can take place automatically.

This object is achieved according to the invention by means of a method having the following steps:
S1 Recording of a mask image with a first modality,
S2 Starting an injection of contrast medium,
S3 Recording of a control image with a second modality,
S4 Image-based determination of the spreading of the contrast medium and analysis for the control of subsequent recordings,
S5 Determining whether a recording criterion has been achieved and, if applicable, repeating steps S3 to S5,
S6 Recording of a contrast image with the first modality,
S7 Processing mask image and contrast image, and
S8 Analyzing processing step S7.

An optimal selection of recording parameters and recording methods is made possible by the automatic triggering of the second recording of an angiography or blood volume measurement on the basis of the analysis of continuously recorded control images.

According to the invention a subtraction and/or an analysis can be performed in processing step S7, the analysis in accordance with processing step S7 possibly being a blood volume measurement.

It has proven advantageous for the control images to be produced with different recording parameters, for example a lower dose, than the mask image.

Advantageously the first modality can be a modality from the following group:
Magnetic resonance tomography (MR angiography),
Computed tomography (CT angiography),
3D angiography (C-arm angiography) and/or
X-ray projection (digital subtraction angiography (DSA)).

It is particularly advantageous if the recordings of the control images are produced using x-ray fluoroscopy.

According to the invention the analysis of processing step S7 in accordance with step S8 can be a visualization of a subtraction image.

The analysis according to step S8 of the processing of mask image and contrast image according to step S7 can advantageously be an automatic analysis of a subtraction image.

It has proven advantageous for the total amount of contrast medium in the volume being observed to be determined as the recording criterion according to step S5 for the degree of spreading of the contrast medium.

In the case of 3D imaging methods it has proven expedient for the amount of contrast medium in the volume being observed to be determined as the recording criterion according to step S5 by summation of the grayscale values across all volume elements.

In the case of projection methods, as a recording criterion according to step S5 for the degree of spreading of the contrast medium it is advantageous for the intensities of $I_f$ and $I_m$ of the mask and contrast-control image to be subtracted from each other and summated across all pixels X in accordance with the following formula:

$$F(t) = \sum_{x=0}^{N} (\ln I_f(x, t) - \ln I_m(x, t))$$

According to the invention the exceeding of a specified threshold by the volume of contrast medium can constitute the recording criterion according to step S5 for the contrast image.

Alternatively the criterion that the volume of contrast medium increases no further can be selected as the recording criterion according to step S5 for the contrast image.

The recording parameters and/or the recording method can be determined advantageously as a function of the analysis according to step S4 for controlling subsequent recordings.

BRIEF DESCRIPTION OF THE DRAWINGS

The invention is described below in more detail with reference to exemplary embodiments shown in the drawing, in which.

DETAILED DESCRIPTION OF THE INVENTION

Figure 1:
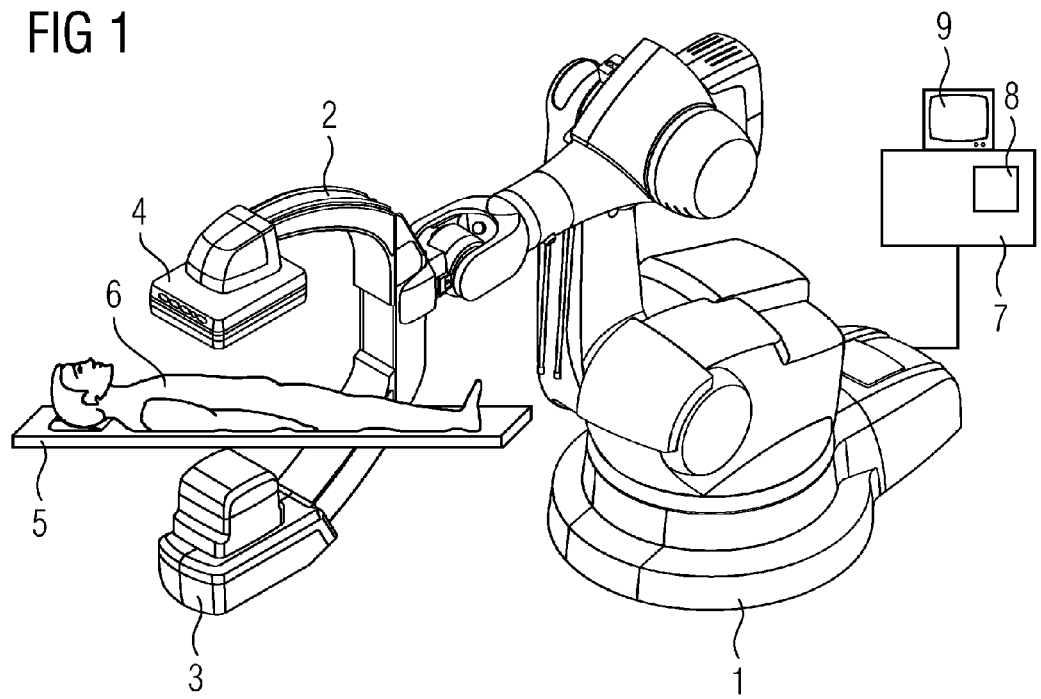
FIG. 1 shows a known x-ray C-arm system with an industrial robot as a support apparatus.

FIG. 1 shows an x-ray diagnostic device for generating C-arm CT recordings, said device having a C-arm 2 mounted rotatably on a stand in the form of an industrial robot 1, with said C-arm having an x-ray radiation source, for example an x-ray emitter 3, and an x-ray image detector 4 arranged at its ends.

The x-ray image detector 4 can be a rectangular or square, flat semiconductor detector that is preferably made of amorphous silicon (a-Si).

A patient 6 to be examined is positioned on a patient positioning couch 5 in the path of the radiation beam of the x-ray emitter 3 for the recording of a heart for example. A system control unit 7 with an imaging system 8 is connected to the x-ray diagnostic device, said imaging system 8 receiving and processing the image signals of the x-ray image detector 4. The x-ray images can then be viewed on a monitor 9.

By means of the industrial robot 1 known for example from DE 10 2005 012 700 A1, which preferably has six axes of rotation and thus six degrees of freedom, the C-arm 2 can be displaced spatially as required, being rotated for example about a center of rotation between the x-ray emitter 3 and (including) the x-ray detector 4. The x-ray system 1 to 4 according to the invention is rotatable in particular about centers of rotation and axes of rotation at the plane of the x-ray image detector 4, preferably about the center of the x-ray image detector 4 and about axes of rotation intersecting the center of the x-ray image detector 4.

Figure 2:
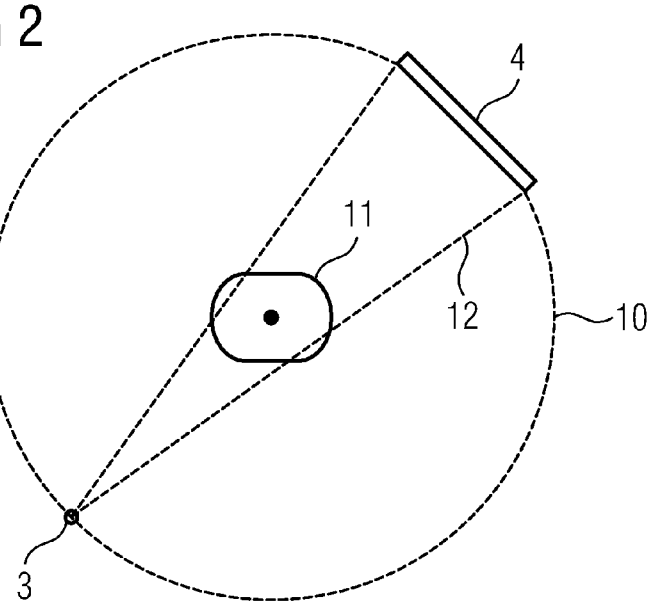
FIG. 2 shows from an axial viewing direction a view of the orbit of a detector and a radiation source according to FIG. 1 about an object to be examined.

If 3D data sets are to be produced in accordance with the so-called DynaCT method known for example from the pamphlet "AXIOM Artis FD Systems/DynaCT—A Breakthrough in Interventional 3D Imaging" by Patrick Kurp, a "Reprint from Medical Solutions, January 2005, pages 46-51", order number A91100-M1400-D105-1-7600, print reference CC 66105 SD 12043, the rotatably mounted C-arm 2 with x-ray emitter 3 and x-ray image detector 4 is rotated such that, as shown schematically in FIG. 2 by the aerial view of the axis of rotation, the x-ray emitter 3 (represented here figuratively by its beam focus) and the x-ray image detector 4 move in an orbit 10 about an object 11 to be examined. In order to produce a 3D data set the orbit 10 can be full or partial.

In accordance with the DynaCT method the C-arm 2 with x-ray emitter 3 and x-ray image detector 4 preferably moves about an angular range of at least 180°, for example 180° plus fan angle, and records projection images in rapid succession from various projections. The reconstruction can be performed using just one section of this recorded data.

The object 11 to be examined can be for example an animal body or a human body or indeed a phantom body.

The x-ray emitter 3 emits a beam of radiation 12 originating from a beam focus of its x-ray radiation source, said beam striking the x-ray image detector 4.

The x-ray emitter 3 and the x-ray image detector 4 each move about the object 5 such that the x-ray emitter 3 and the x-ray image detector 4 are positioned at opposite sides of the object 11.

In normal radiography or fluoroscopy by means of an x-ray diagnostic device of this type the medical 2D data of the x-ray image detector 4 may be buffered in the imaging system and subsequently displayed on the monitor 9.

Figure 3:
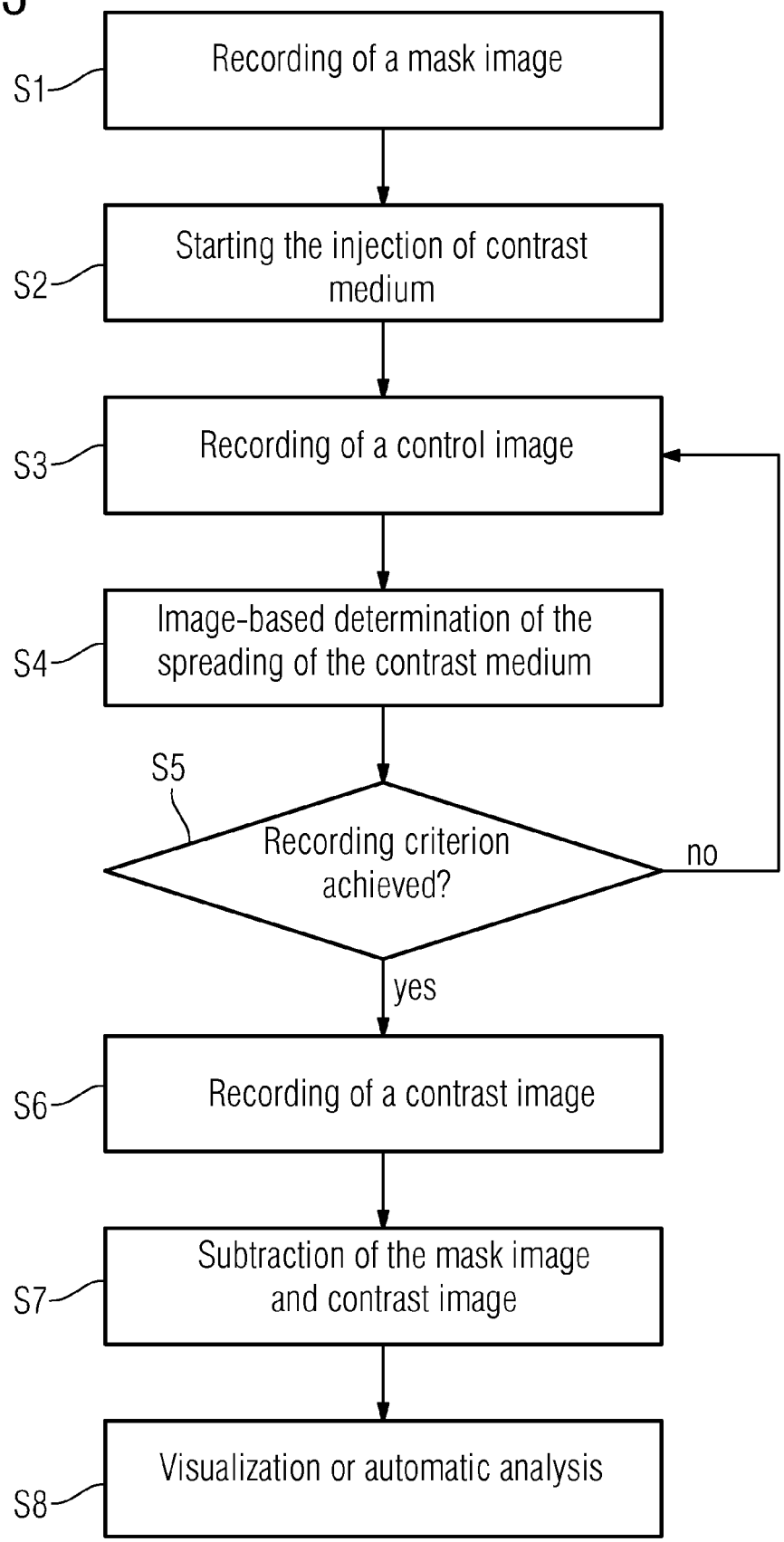
FIG. 3 shows the flow of the method according to the invention.

FIG. 3 illustrates the steps involved in producing an angiography recording. In the first step S1 a mask image is recorded. These recordings can have been produced with the aid of the following recording methods, for example:

Magnetic resonance tomography (MR angiography),
Computed tomography (CT angiography),
3D angiography (C-arm angiography) and/or
X-ray projection (digital subtraction angiography (DSA)).

The injection of contrast medium commences in the second step S2. Next a control image is recorded in the third step S3 by means of x-ray radiation. In the fourth step S4 an image-based determination of the spreading of the contrast medium is performed in this control image. In the subsequent fifth step S5 it is determined whether the recording criterion has been achieved. If this is not the case, a recording of a control image is performed in addition to that recorded in step S3, until the recording criterion is achieved. If this is the case a contrast image is recorded in the sixth step S6, which image is fed in the seventh step S7 to a subtraction function in which the mask image produced in the first step is subtracted from the contrast image. In the eighth step S8 a visualization is finally output on a display or an automatic analysis of the subtraction image is performed.

Figure 4:
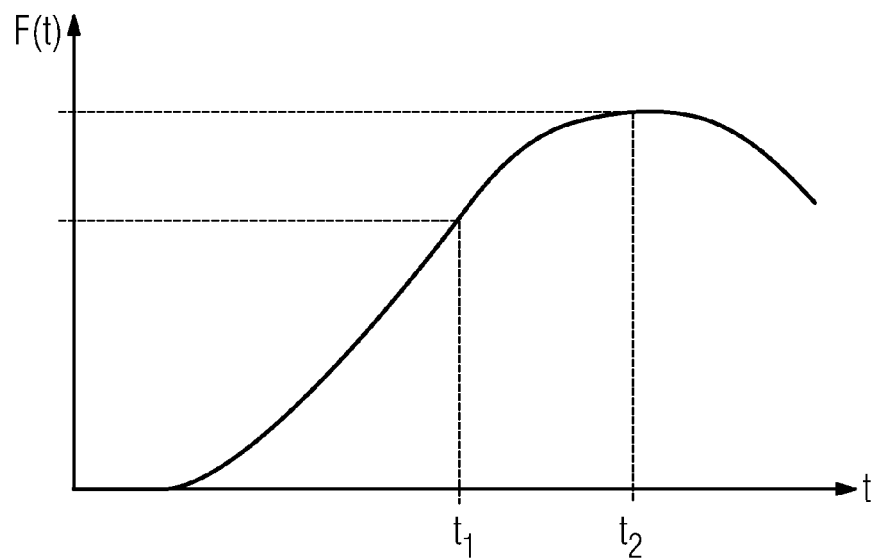
FIG. 4 shows the trend in the volume of contrast medium as functions F(t) over time t.

The recording criterion mentioned in FIG. 3 can be for example that the volume of contrast medium, the trend of which is shown in FIG. 4 as functions F(t) over time t, exceeds a specified threshold. This can be for example the threshold S that has been achieved at the time $t_1$. However the recording criterion can also be fulfilled if the volume of contrast medium does not increase any further, as is the case at time $t_2$.

By means of the method according to the invention the contrast recordings of an angiography, based on the image-based analysis of control images, can be triggered automatically.

A method of this type has the following advantages:

Patient-specific variances in the spreading of the contrast medium are taken into consideration and consequently the number of erroneous recordings is reduced, Manual test injections can be avoided in particular in the case of venous injections, since a more precise and more rapid determination of the spreading of the contrast medium can be achieved than is the case by human observers, and Newer sensitive recording methods are made possible as a result, for example the measurement of cerebral blood volume (CBV).

The method according to the invention is conceivable in the widest possible range of combinations of recording technologies, such as those specified schematically by way of examples in the following three combinations.

Figure 5:
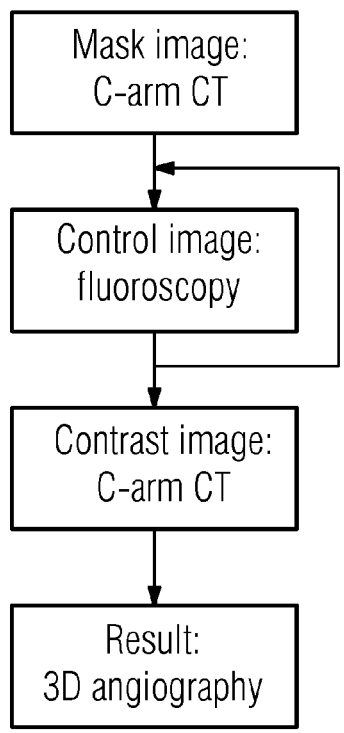
FIGS. 5 to 7 show different possible combinations of different recording technologies.

FIG. 5 represents a first example of a recording technology. The mask image is produced by means of C-arm CT. The control image is monitored using fluoroscopy. The contrast image is in turn recorded by means of C-arm CT and the result is a recording in 3D angiography.

Figure 6:
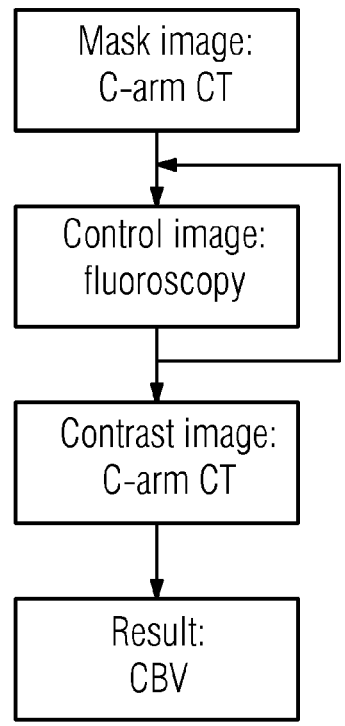

FIG. 6 shows a second example of a recording technology. A C-arm CT recording is again used as the mask image. The control is again performed by means of fluoroscopy. The contrast image is also a C-arm CT recording. However no subtraction image is produced from these images, but instead the spreading of the contrast medium is determined and a measurement of the cerebral blood volume (CBV) is performed.

Figure 7:
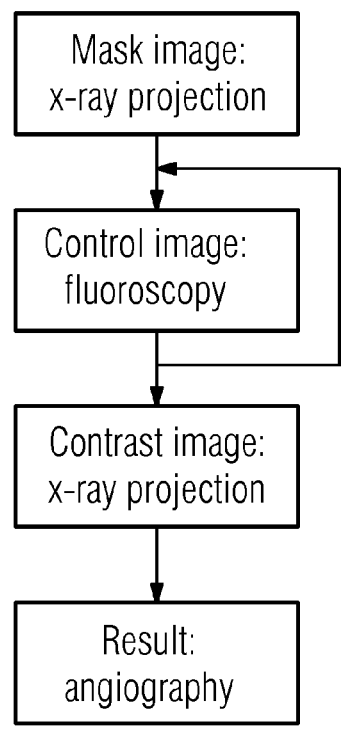

FIG. 7 illustrates an example of a further recording technology. In this case an x-ray projection is used as the mask image. The control images are again produced by means of fluoroscopy. An x-ray projection is used as a contrast image, the result of which is a normal angiography recording.

The method according to the invention serves for automatically triggering the second recording of an angiography or blood volume measurement on the basis of the analysis of continuously recorded control images. Here the control images can be generated using different recording parameters (for example a lower dose) or a completely different recording method (for example x-ray fluoroscopy to record a control image for 3D angiography) than the angiography recordings themselves. The aim here is to generate the control images using a method that enables the spreading of the contrast medium to be determined within the best possible time interval and with minimal exposure for the patient (e.g. in terms of x-ray dose), and consequently to identify the ideal time for the angiography recording, which is then performed using a method that provides the best possible answers to the clinical questions.

The sequence of steps according to the invention for producing the angiography recording is as follows:

Recording of a mask image,
Starting the injection of contrast medium,
Image-based determination of the spreading of the contrast medium,
Recording of a contrast image,
Subtraction of the mask image and contrast image, and
Visualization or automatic analysis.

The total amount of contrast medium in the volume being observed can be determined as a criterion for the degree of spreading of the contrast medium.

In the case of 3D imaging methods the amount of contrast medium in the volume being observed can be determined by summation across all volume elements, if it is assumed that the grayscale values of a voxel have a linear relationship with the concentration of contrast medium.

On the other hand, in the case of projection methods the intensities of $I_f$ and $I_m$ in the mask image and contrast image are subtracted from each other and summated across all pixels X:

$$F(t) = \sum_{x=0}^{N} (\ln I_f(x, t) - \ln I_m(x, t))$$

The sum F then corresponds to the amount of contrast medium except for an unknown multiplicative constant. Depending on the type of imaging the constant can be determined analytically, by simulation or by calibration measurements.

The recording criterion for the contrast image can be for example that the volume of contrast medium exceeds a specified threshold (see figure, time $t_1$) or that the volume of contrast medium increases no further (see figure, time $t_2$).

In the method according to the invention a control of subsequent recordings (in terms of parameters and recording methods) takes place as a function of the analysis. The online analysis of an "x-ray image being observed" is used to control the timing of the actual "recordings". Not only different recording parameters but also entirely different recording methods can be used here. Provision is made in particular for the combination of 2D and 3D methods, examples of which are given in the following table.

| Online observation - control image | Recording - mask image and contrast image |
| --- | --- |
| 2D x-ray examination - fluoroscopy | 3D rotation scan - C-arm CT |
| MR angiography | MR angiography |
| CT fluoro | CT spiral scan |
| 2D ultrasound | 3D rotation scan |
| 2D ultrasound | MR angiography |
| 2D ultrasound | CT spiral scan |

The invention claimed is:

1. A method for a production of an angiography recording of a patient, comprising in the following order:

recording a mask image of the patient with a first imaging modality without a contrast medium;

starting an injection of a contrast medium into the patient;

recording a control image of the patient with the contrast medium using a second imaging modality;

determining a spreading of the contrast medium in the patient based on the control image;

checking whether a recording criterion has been achieved from the spreading of the contrast medium;

repeatedly recording the control image and determining the spreading of the contrast medium if the recording criterion has not been achieved;

recording a contrast image of the patient with the contrast medium using the first imaging modality when the recording criterion has been achieved;

processing the mask image and the contrast image; and analyzing the processed mask image and the processed contrast image for the production of the angiography recording of the patient.

2. The method as claimed in claim 1, wherein the processing step comprises generating a subtraction image of the mask image and the contrast image.

3. The method as claimed in claim 1, wherein the processing step comprises an analysis of the patient.

4. The method as claimed in claim 3, wherein the analysis is a blood volume measurement.

5. The method as claimed in claim 1, wherein the control image is recorded using different recording parameters than the mask image.

6. The method as claimed in claim 1, wherein the first imaging modality is selected from the group consisting of: Magnetic resonance tomography, Computed tomography, 3D angiography, and X-ray projection.

7. The method as claimed in claim 6, wherein the second imaging modality is an x-ray fluoroscopy.

8. The method as claimed in claim 1, wherein the analyzing step comprises a display of a subtraction image of the mask image and the contrast image generated in the processing step.

9. The method as claimed in claim 1, wherein the analyzing step comprises an automatic analysis of a subtraction image of the mask image and the contrast image generated in the processing step.

10. The method as claimed in claim 1, wherein the recording criterion is an amount of the contrast medium in a volume for a degree of the spreading of the contrast medium.

11. The method as claimed in claim 10, wherein for a 3D imaging method, the amount of the contrast medium in the volume is determined by summing grayscale values across all volume elements.

12. The method as claimed in claim 10, wherein for a projection method, the amount of the contrast medium in the volume is determined by subtracting an intensity $I_f$ of the mask image and an intensity $I_m$ of the control image and summing across all pixels X with the following formula:

$$F(t) = \sum_{x=0}^{N} (\ln I_f(x, t) - \ln I_m(x, t)).$$

13. The method as claimed in claim 1, wherein the recording criterion is an amount of the contrast medium in a volume when exceeding a specified threshold.

14. The method as claimed in claim 1, wherein the recording criterion is an amount of the contrast medium in a volume when having no further increasing.

15. The method as claimed in claim 1, wherein the subsequent recordings are controlled by recording parameters or recording methods.

16. An image diagnostic device, comprising:
a first imaging modality that records:
  a mask image of a patient before an injection of a contrast medium, and
  a contrast image of the patient after the injection of the contrast medium when a recording criterion has been achieved;
a second imaging modality that records a control image of the patient after the injection of the contrast medium; and
a control unit that:
  determines a spreading of the contrast medium and analyzes a control of subsequent recordings based on the control image;
  checks whether the recording criterion has been achieved from the spreading of the contrast medium;
  automatically controls the first imaging modality to record the contrast image when the recording criterion has been achieved;
  subtracts the mask image from the contrast image; and
  analyzes the processed mask image and the processed contrast image.

* * * * *